US008372609B2

(12) United States Patent
Sabesan

(10) Patent No.: US 8,372,609 B2
(45) Date of Patent: Feb. 12, 2013

(54) PROCESS FOR PRODUCING A SUGAR SOLUTION BY COMBINED CHEMICAL AND ENZYMATIC SACCHARIFICATION OF POLYSACCHARIDE ENRICHED BIOMASS

(75) Inventor: Subramaniam Sabesan, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 714 days.

(21) Appl. No.: 12/621,585

(22) Filed: Nov. 19, 2009

(65) Prior Publication Data

US 2010/0124772 A1 May 20, 2010

Related U.S. Application Data

(60) Provisional application No. 61/116,388, filed on Nov. 20, 2008.

(51) Int. Cl.
- *C08B 37/00* (2006.01)
- *C07H 1/00* (2006.01)
- *C07H 1/06* (2006.01)
- *C07H 1/08* (2006.01)
- *C07H 3/00* (2006.01)
- *C13K 5/00* (2006.01)
- *C13K 7/00* (2006.01)
- *C12P 1/00* (2006.01)
- *C12P 7/00* (2006.01)
- *C12P 19/00* (2006.01)
- *C12P 19/04* (2006.01)
- *C12S 3/02* (2006.01)
- *C12S 3/04* (2006.01)

(52) U.S. Cl. ........ 435/132; 435/267; 435/966; 536/123; 536/123.1; 536/123.12; 536/123.13; 536/124; 536/127; 536/128

(58) Field of Classification Search .................. None
See application file for complete search history.

(56) References Cited

U.S. PATENT DOCUMENTS

| | | | |
|---|---|---|---|
| 3,844,890 A * | 10/1974 | Horikoshi et al. | 435/209 |
| 4,072,538 A | 2/1978 | Fahn et al. | |
| 4,237,110 A | 12/1980 | Forster et al. | |
| 4,645,658 A | 2/1987 | Gaddy et al. | |
| 4,904,599 A * | 2/1990 | Ozaki et al. | 435/252.33 |
| 4,962,030 A * | 10/1990 | Kawai et al. | 435/209 |
| 5,188,673 A | 2/1993 | Clausen et al. | |
| 5,196,069 A | 3/1993 | Cullingford et al. | |
| 5,407,827 A * | 4/1995 | Casimir-Schenkel et al. | 435/278 |
| 5,503,996 A | 4/1996 | Torget et al. | |
| 5,726,046 A | 3/1998 | Farone et al. | |
| 5,916,780 A | 6/1999 | Foody et al. | |
| 6,090,595 A | 7/2000 | Foody et al. | |
| 6,376,445 B1 * | 4/2002 | Bettiol et al. | 510/320 |
| 6,752,902 B2 | 6/2004 | Heikkila et al. | |
| 7,354,743 B2 | 4/2008 | Vlasenko et al. | |
| 7,807,021 B2 * | 10/2010 | Blackstone et al. | 162/80 |
| 2004/0231060 A1 | 11/2004 | Burdette et al. | |
| 2007/0031918 A1 * | 2/2007 | Dunson et al. | 435/41 |
| 2009/0317871 A1 * | 12/2009 | Kim et al. | 435/71.2 |
| 2010/0024810 A1 | 2/2010 | Harmer et al. | |
| 2010/0035318 A1 | 2/2010 | MeloSantanna et al. | |
| 2010/0124770 A1 * | 5/2010 | Sabesan et al. | 435/101 |
| 2010/0143974 A1 * | 6/2010 | Chung et al. | 435/72 |

FOREIGN PATENT DOCUMENTS

| | | |
|---|---|---|
| WO | 0237981 A2 | 5/2002 |
| WO | 2004081185 A2 | 9/2004 |
| WO | 2008/065433 A1 | 6/2008 |
| WO | 2008095098 A2 | 8/2008 |
| WO | 2008134037 A1 | 11/2008 |

OTHER PUBLICATIONS

Borjesson, Johan et al., Enhanced enzymatic conversion of softwood lignocellulose by poly(ethylene glycol) addition, Enzyme and Microbial Technology, 2007, pp. 754-762, vol. 40, Elsevier Inc.

Qiabi, A. et al., Comparative studies of hemicellulose hydrolysis processes: application to various lignocellulosic wastes, Industrial Crops and Products, 1994, pp. 95-102, vol. 3, Elsevier Science B.V.

Brief Description of Electroep's Mild-Pretreatment Process for Cellulosic Biofuels, Oct. 23, 2008, Electrostep, Inc., Corvallis, Oregon.

Al-Ani, F. et al., Effect of Chemical Pretreatments on the Fermentation and Ultimate Digestibility of Bagasse by *Phanerochaete chrysosporium*, Journal of the Science of Food and Agriculture, 1988, pp. 19-28, vol. 42, Society of Chemistry Industry.

Tewari, Harmesh K. et al., Role of Pretreatments on Enzymatic Hydrolysis of Agricultural Residues for Reducing Sugar Production, Journal of Chemical Technology and Biotechnology, 1987, pp. 153-165, vol. 38, No. 38, Society of Chemical Industry.

Akhtar, Muhammad Saleem et al., Saccharification of Lignocellulosic Materials by the Cellulases of *Bacillus subtilis*, International Journal of Agriculture & Biology, 2001, pp. 199-202, vol. 3, No. 2.

Archibald, J. G., The Effect of Sodium Hydroxid on the Composition, Digestibility, and Feeding Value of Grain Hulls and Other Fibrous Material, Journal of Agricultural Research, Feb. 2, 1924, pp. 245-265, vol. 27, No. 5.

Singh, A. et al., Saccharification of cellulosic substrates by *Aspergillus niger* cellulase, World Journal of Microbiology and Biotechnology, 1990, pp. 333-336, vol. 6, Rapid Communications of Oxford Ltd.

Hsu, Wen-Hui et al., A new alkali process for the treatment of agricultural byproducts, Shipin Gongye, 1978, vol. 10, No. 1, Food. Ind. Res. Dev. Inst., Hsinchu, Taiwan (Abstract attached).

Teixeira, Lincoln. C. et al., Alkaline and Peracetic Acid Pretreatments of Biomass for Ethanol Production, Applied Biochemistry and Biotechnology, 1999, pp. 19-34, vol. 77-79, Human Press Inc.

Elshafei, Ali M. et al., The Saccharification of Corn Stover by Cellulase from *Penicillium funiculosum*, Bioresource Technology, 1991, pp. 73-80, vol. 35, Elsevier Science Publishers Ltd.

Kim, Tae Hyun et al., Pretreatment and fractionation of corn stover by ammonia recycle percolation process, Bioresource Technology, 2005, pp. 2007-2013, vol. 96, Elsevier Ltd.

\* cited by examiner

*Primary Examiner* — Debbie K Ware

(57) ABSTRACT

Concentrated sugar solutions obtained from polysaccharide enriched biomass by contacting biomass with water and at least one nucleophilic base to produce a polysaccharide enriched biomass comprising a solid fraction and a liquid fraction and then contacting enriched biomass with a dilute mineral acid selected from the group consisting of sulfuric acid, phosphoric acid, hydrochloric acid, nitric acid, or a combination thereof, to produce an intermediate saccharification product, which is contacted with an enzyme consortium to produce a final saccharification product comprising fermentable sugars.

13 Claims, No Drawings

PROCESS FOR PRODUCING A SUGAR SOLUTION BY COMBINED CHEMICAL AND ENZYMATIC SACCHARIFICATION OF POLYSACCHARIDE ENRICHED BIOMASS

CROSS-REFERENCE TO RELATED APPLICATIONS

This application claims benefit of Provisional Application No. 61/116,388 filed Nov. 20, 2008. This application hereby incorporates by reference Provisional Application No. 61/116,388 in its entirety.

FIELD OF THE INVENTION

Methods for treating biomass to obtain concentrated, fermentable sugar solutions are provided. Specifically, polysaccharide enriched biomass is obtained by the pretreatment of biomass with at least one nucleophilic base in a manner which retains the glucan/xylan weight ratio of the untreated biomass. Concentrated sugar solutions are obtained by combined chemical and enzymatic saccharification of the polysaccharide enriched biomass.

BACKGROUND

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as fuels and other chemicals. Cellulosic and lignocellulosic feedstocks and wastes, composed of carbohydrate polymers comprising cellulose, hemicellulose, and lignin are generally treated by a variety of chemical, mechanical and enzymatic means to release primarily hexose and pentose sugars, which can then be fermented to useful products.

Pretreatment methods are used to make the carbohydrate polymers of cellulosic and lignocellulosic materials more readily available to saccharification enzymes. Standard pretreatment methods have historically utilized primarily strong acids at high temperatures; however due to high energy costs, high equipment costs, high pretreatment catalyst recovery costs and incompatibility with saccharification enzymes, alternative methods are being developed, such as enzymatic pretreatment, or the use of acid or base at milder temperatures where decreased hydrolysis of biomass carbohydrate polymers occurs during pretreatment, requiring improved enzyme systems to saccharify both cellulose and hemicellulose.

Teixeira, L., et al. (Appl. Biochem. and Biotech. (1999) 77-79:19-34) disclosed a series of biomass pretreatments using stoichiometric amounts of sodium hydroxide and ammonium hydroxide, with very low biomass concentration. The ratio of solution to biomass is 14:1.

Elshafei, A. et al. (Bioresource Tech. (1991) 35:73-80) examined the pretreatment of corn stover utilizing NaOH.

Kim, T. and Y. Lee (Bioresource Technology (2005) 96:2007-2013) report the use of high amounts of aqueous ammonia for the pretreatment of corn stover.

Int'l. Pat. App. Pub. No. WO2004/081185 discusses methods for hydrolyzing lignocellulose, comprising contacting the lignocellulose with a chemical; the chemical may be a base, such as sodium carbonate or potassium hydroxide, at a pH of about 9 to about 14, under moderate conditions of temperature, pressure and pH.

U.S. Pat. Nos. 5,916,780 and 6,090,595, describe a pretreatment process wherein a specified ratio of arabinoxylan to total nonstarch polysaccharides (AX/NSP) is assessed and used to select the feedstock.

U.S. Pat. No. 5,196,069 discloses a process for converting cellulosic waste into soluble saccharide by irradiating an aqueous cellulose feed mixture with microwave radiation in the presence of acetic acid at an elevated pressure, the efficiency obtained from an enzymatic hydrolysis is greatly enhanced.

Most pretreatments such as the ones described above either result in a pretreated biomass depleted of lignin and hemicellulose or the partial depletion of hemicellulose with retention of most of the lignin. Therefore a method is needed to selectively remove only lignin without significant loss of either hemicellulose or cellulose from the biomass, as these constitute the source of sugars for fermentation.

Most approaches to converting polysaccharides to a source of fermentable sugars have relied on the use of either acid catalyzed hydrolysis or enzymatic saccharification for the hydrolysis of xylans and glucans to monosaccharides. The acid-only based approach suffers from both the low yield often seen in acid-catalyzed hydrolysis and also the generation of byproducts which can be detrimental to down stream processing steps, such as fermentation. This arises from the vast difference in the kinetics of hydrolysis of xylans and glucans, which are more difficult and easier to hydrolyze, respectively. The difference in stability of the sugars when heated under acidic conditions is also a drawback to the acid-only approach. Furthermore, the presence of acid or its salt, especially of organic acids, can result in lower performance of fermentation enzymes, necessitating the removal of the organic acid or its salt prior to the fermentation of the hydrolyzate. The enzyme-based approach suffers from the high cost associated with enzymes and the recalcitrance of the biomass to undergo quantitative saccharification. A method of converting polysaccharides to monosaccharides which overcomes these difficulties is needed.

SUMMARY

Described herein are methods of producing a concentrated sugar solution from polysaccharide enriched biomass containing both hemicellulose and cellulose. These methods include a pretreatment step in which biomass is contacted with water and at least one nucleophilic base, with subsequent change in pH from the range of about 12.5-13.0 to the range of about 9.5-10. During pretreatment, the lignin is solubilized and the glucan/xylan weight ratio in the insoluble biomass is largely retained, compared to that for untreated biomass. The solid fraction of the resulting polysaccharide enriched biomass is contacted as an aqueous suspension with dilute mineral acid under low concentrations that are not detrimental to saccharification or fermentation enzymes, in order to selectively hydrolyze greater than 50% of the hemicellulose in the polysaccharide enriched biomass, also known as the carbohydrate-enriched biomass. This is then allowed to react with a saccharification enzyme consortium comprising cellulose hydrolyzing enzymes to produce a final saccharification product.

The methods described herein include a method of producing a concentrated sugar solution from biomass, the method comprising:

a) delignifying biomass comprising the substeps of
   i) contacting with water and at least one nucleophilic base, a biomass comprising lignin and having a glucan/xylan weight ratio $G_1/X_1$ to form a biomass slurry having a pH of about 12.5 to about 13.0; and ii) maintaining the biomass slurry under reaction conditions such that the slurry attains a pH of about 9.5 to about 10.0 and has a a glucan/xylan weight ratio $G_2/X_2$ within about 15% of the value of $G_1/X_1$, and wherein the slurry comprises a lignin-containing liquid fraction and a solid fraction comprising a polysaccharide enriched biomass;

wherein $G_1$ and $G_2$ are grams of glucan per 100 grams of biomass and biomass slurry respectively, and $X_1$ and $X_2$ are grams of xylan per 100 grams of biomass and biomass slurry respectively;

b) contacting with an aqueous acid solution comprising at least one mineral acid the solid fraction of the polysaccharide enriched biomass at reaction conditions sufficient to produce an intermediate saccharification product comprising xylose, xylan, and glucan, wherein the concentration of the solid fraction in the aqueous acid solution is about 13 weight percent to about 20 weight percent; and c) contacting with a saccharification enzyme consortium at a pH of from about 4.5 to about 5.5 the intermediate saccharification product at reaction conditions sufficient to produce a final saccharification product comprising at least about 7 percent by weight fermentable sugars, based on the total weight of the saccharification product, in 24 hours of contact with the saccharification enzyme consortium.

Biomass refers to any cellulosic or lignocellulosic material, for example, bioenergy crops, agricultural residues, municipal solid waste, industrial solid waste, yard waste, wood, forestry waste, and combinations of these.

In these methods, the at least one nucleophilic base comprises a water soluble metal hydroxide, optionally in combination with a metal carbonate or an organic hydroxide. The reaction conditions to produce a polysaccharide enriched biomass may include a temperature from about 20° C. to about 110° C. and the reaction time may be from about 4 hours to about 30 days. The value of $G_2/X_2$ may be within 10% of the value of $G_1/X_1$.

At least a portion of the polysaccharide enriched biomass solid fraction may be isolated by filtration. The composition of the isolated polysaccharide enriched biomass solid fraction, on a dry weight basis, may be greater than about 80% polysaccharide.

The at least one mineral acid is selected from the group consisting of sulfuric acid, phosphoric acid, hydrochloric acid, nitric acid, or a combination of these. The concentration of the mineral acid in the aqueous acid solution may be about 0.1 weight percent to about 5 weight percent. The reaction conditions to produce an intermediate saccharification product may include a temperature from about 70° C. to about 160° C. and a reaction time from about 10 minutes to about 200 minutes.

At least about 50 percent of the xylan in the isolated polysaccharide enriched biomass may be hydrolyzed in the intermediate saccharification product. The final saccharification product may comprise at least about 12 percent by weight sugars in 72 hours. The final saccharification product comprises at least one sugar monomer selected from the group consisting of glucose, arabinose, xylose, mannose, and galactose, and a combination of these.

DETAILED DESCRIPTION OF THE INVENTION

Definitions

The methods described herein are described with reference to the following terms.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "invention" or "present invention" as used herein is a non-limiting term and is not intended to refer to any single variation of the particular invention but encompasses all possible variations described in the specification and recited in the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination of these. Biomass that is useful for the invention may include biomass that has a relatively high carbohydrate value, is relatively dense, and/or is relatively easy to collect, transport, store and/or handle. In one embodiment of the invention, biomass that is useful includes corn cobs, corn stover, sawdust, and sugar cane bagasse.

As used herein, the term "lignocellulosic" refers to a composition comprising both lignin and cellulose. Lignocellulosic material may also comprise hemicellulose.

As used herein, the term "cellulosic" refers to a composition comprising cellulose.

As used herein, by "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

As used herein, the terms "target chemical" and "target product" are interchangeable and refer to a chemical, fuel, or chemical building block produced by fermentation. Chemical or product is used in a broad sense and includes molecules such as proteins, including, for example, peptides, enzymes, and antibodies. Also contemplated within the definition of target product are ethanol and butanol.

As used herein, the term "saccharification" refers to the hydrolysis of polysaccharides to their constituent monomers and/or oligomers.

As used herein, the term "intermediate saccharification product" refers to the product comprising xylose, xylan, and glucan obtained by contacting the solid fraction of polysaccharide enriched biomass with an aqueous acid solution comprising at least one mineral acid. An intermediate saccharification product will contain relatively more monomeric xylose than a final saccharification product does.

As used herein, the term "final saccharification product" refers to the product comprising fermentable sugars obtained by contacting the intermediate saccharification product with a saccharification enzyme consortium.

As used herein, the term "polysaccharide enriched biomass" means biomass that has been subjected to pretreatment prior to saccharification such that the noncarbohydrate component of the biomass is significantly reduced.

As used herein, "readily saccharifiable biomass" means biomass that is carbohydrate-enriched and made more amenable to hydrolysis by cellulolytic or hemi-cellulolytic enzymes for producing monomeric and oligomeric sugars. The term "readily saccharifiable biomass" as used herein is interchangeable with the term "solid fraction of the polysaccharide enriched biomass".

As used herein, the term "carbohydrate-enriched" as used herein refers to the biomass produced by the process treatments described herein. The terms polysaccharide enriched and carbohydrate-enriched are interchangeable. In one embodiment the readily saccharifiable carbohydrate-enriched biomass produced by the processes described herein have a carbohydrate concentration of greater than or equal to about 85% of the biomass carbohydrate as compared to biomass prior to pretreating as described herein while removing 75% or greater of the biomass lignin.

As used herein, the term "loading of the enzyme consortium" and "enzyme loading" are interchangeable and refer to a ratio of the amount total weight of protein in the enzyme consortium relative to the weight of polysaccharide enriched biomass.

As used herein, the terms "delignification" refers to any process by which lignin is either partly, mostly or wholly removed from cellulosic materials. Generally, this process is by means of chemical treatment. The residue that remains consists of cellulose, hemicelluloses, and other carbohydrate materials. Any residue having undergone a delignification is described herein as "delignified". As used herein, "lignin" refers generally to a polymer found extensively in the cell walls of all woody plants.

As used herein, the term "cellulase" refers to polysaccharide-hydrolyzing enzymes that can exhibit an activity, such as cellulose degradation, that may be several enzymes or a group of enzymes having different substrate specificities. Thus, a cellulase from a microorganism may comprise a group of enzymes, all of which may contribute to the cellulose-degrading activity.

As used herein, the terms "nucleophile" and "nucleophilic base" refer to a Lewis base (as that term is used in the art) that is a reagent that forms a chemical bond to its reaction partner, the electrophile, by donating both bonding electrons. Most bases are also nucleophiles. (See for example *Organic Chemistry*, $7^{th}$ *Edition*, Morrison, Robert Thornton; Boyd, Robert N., (1998) Publisher: (Prentice Hall, Englewood Cliffs, N.J.). For example, in the methods described herein, the nucleophile NaOH reacts and forms chemical bonds with lignin and its components.

Pretreatment (Delignification)

In the methods described herein, biomass is contacted with water and at least one nucleophilic base to form a biomass slurry having an initial pH of about 12.5 to about 13.0. The provided biomass has a glucan/xylan weight ratio $G_1/X_1$, where $G_1$ is the grams of glucan per 100 grams of biomass and $X_1$ is the grams of xylan per 100 grams of biomass. Glucan and xylan content of biomass can be determined by methods known in the art. The source of the biomass is not determinative of the invention and the biomass may be from any source.

The biomass slurry is maintained at a temperature and for a reaction time sufficient to produce a polysaccharide enriched biomass having a glucan/xylan weight ratio $G_2/X_2$, where $G_2$ is the grams of glucan per 100 grams of polysaccharide enriched biomass and $X_2$ is the grams of xylan per 100 grams of polysaccharide enriched biomass. In contrast to other pretreatment methods, the polysaccharide enriched biomass is produced without selective loss of xylan, as evidenced by a comparison of the values of the ratios $G_2/X_2$ and $G_1/X_1$. Similarity of the numerical values for the glucan/xylan weight ratios of the treated and the untreated biomass indicate that both glucan and xylan are retained in about the same relative amounts in the polysaccharide enriched biomass as were present in the biomass before pretreatment.

The value of $G_2/X_2$ may be within about 15% or within about 10% of the value of $G_1/X_1$. Avoiding preferential loss of xylan during the pretreatment step provides higher xylose yield after saccharification and contributes to improved sugar yields overall and higher sugar concentrations.

The pretreated biomass is referred to as "polysaccharide enriched biomass" because the pretreatment described above, and in more detail below, solubilizes the lignin contained in the biomass. The glucan and xylan remain insoluble. Physical separation of the lignin-containing liquid fraction from the solid fraction removes lignin and provides solid polysaccharide enriched biomass.

Delignifying biomass prior to enzymatic hydrolysis (saccharification) is advantageous as lignin can bind non-specifically to saccharification enzymes. Removal of lignin before saccharification enables the use of lower enzyme loadings, which provides cost savings with regard to enzyme usage. Removing lignin before saccharification can also improve saccharification rate, titer, and yield. Furthermore, as lignin can contribute to increased viscosity of biomass and biomass slurry, removal of lignin can provide reduced viscosity of biomass and slurries containing biomass, thereby enabling very high loading, for example, greater than about 20 percent, of the biomass in order to produce a concentrated sugar syrup.

The biomass may be used directly as obtained from the source, or energy may be applied to the biomass to reduce the size, increase the exposed surface area, and/or increase the availability of cellulose, hemicellulose, and/or oligosaccharides present in the biomass to the nucleophilic base and to saccharification enzymes and/or additive used in the saccharification step. Energy means useful for reducing the size, increasing the exposed surface area, and/or increasing the availability of cellulose, hemicellulose, and/or oligosaccharides present in the biomass include, but are not limited to, milling, crushing, grinding, shredding, chopping, disc refining, ultrasound, and microwave. This application of energy may occur before or during pretreatment, before and during saccharification, or any combination of these.

In general, it is often required to mill the biomass before and/or after pretreatments in order to reduce the particle size and to produce high surface area and porous particles for effective enzymatic saccharification. In the methods described here, we unexpectedly find that this energy intensive milling process can be avoided, as the nucleophilic base treatment under selected conditions results in chemical milling to provide delignified biomass of substantially reduced particle size.

The biomass is contacted with water sufficient to wet the entire biomass and at least one nucleophilic base comprising a water soluble metal hydroxide, such as sodium hydroxide or potassium hydroxide. The water soluble metal hydroxide may be used alone or in combination with a metal carbonate, such as sodium carbonate or potassium carbonate, or an organic hydroxide, such as ammonium or alkyl substituted ammonium hydroxides. The nucleophilic base is combined as an aqueous solution or as a solid with the biomass and water to form a biomass slurry having an initial pH of about 12.5 to about 13.0. As the delignification proceeds, some of the base is consumed and the pH of the biomass slurry is reduced to a range of about 9.5 to about 10.0. A sufficient concentration of base should be used such that the pH does not drop lower, which would result in insufficient delignification. The extent of delignification may depend at least in part on the choice of reaction conditions and the type of biomass used. For example, in the case of corn cob, about 8 weight percent of NaOH relative the weight of the corn cob has been found to provide optimum delignification. In some of the methods described herein, at least about 70 percent or at least about 80 percent or at least about 90 percent of the lignin in the provided biomass may be delignified in the isolated polysaccharide enriched biomass.

The amount of water in the biomass slurry may be from about 25 weight percent to about 90 weight percent, for example from about 50 weight percent to about 90 weight percent, or from about 75 weight percent to about 90 weight percent based on the combined weight of the biomass, the water, and the nucleophilic base. The water in the biomass slurry refers to the total water from all sources and includes any water contained in or on the biomass, water contained in an aqueous solution of the nucleophilic base, and water added separately.

The dry weight of biomass in the biomass slurry may be at an initial concentration from about 10 weight percent to about 75 weight percent, or for example from about 10 weight percent to about 50 weight percent, or for example from about 10 weight percent to about 25 weight percent, based on the combined weight of the biomass, the water, and the nucleophilic base. The biomass concentration may be maximized to the extent possible to minimize the volume of the reaction vessel. The high biomass concentration also reduces the total volume of pretreatment material, making the process more economical. From a practical viewpoint, high ratios of the weight of biomass to the weight of the basic solution can be limited by the ability to provide sufficient mixing, or intimate contact, for pretreatment to occur at a practical rate.

The biomass slurry is maintained at a temperature of from about 20° C. to about 110° C., for example from about 80° C. to about 110° C. The contacting of the biomass with water and at least one nucleophilic base may be carried out for a period time from about 4 hours to about 30 days, for example from about 4 hours to about 1 day. Longer periods of pretreatment are possible; however a shorter period of time may be preferable for practical, economic reasons. Typically a period of contact may be about 24 hours or less and is determined by the time required for the pH of the biomass slurry to drop from a range of about 12.5 to 13.0 to a range of about 9.5 to 10.0.

The delignification of biomass with water and at least one nucleophilic base may be performed at a relatively high temperature for a relatively short period of time, for example at from about 90° C. to about 100° C. for about 24 hours to about 16 hours. Or, the biomass-nucleophilic base contacting process may be performed at a lower temperature for a longer period of time, for example from about 50° C. to about 80° C. for about 140 hours to about 100 hours. Or, the biomass-acid contacting process may be performed at room temperature (approximately 22-25° C.) for a period of time up to about 300 hours. Other temperature and time combinations intermediate to these may also be used.

For the contacting of the biomass with water and at least one nucleophilic base, the temperature, reaction time, base concentration, weight percent of total water, the biomass concentration, the biomass type, and the biomass particle size are related; thus these variables may be adjusted as necessary to obtain sufficient delignification rate in a controllable manner and to obtain an optimal product for saccharification to sugars.

The pretreatment may be performed in any suitable vessel, such as a batch reactor a continuous reactor. The suitable vessel may be equipped with a means, such as impellers, for agitating the biomass/acid mixture. Reactor design is discussed in Lin, K.-H., and Van Ness, H. C. (in Perry, R. H. and Chilton, C. H. (eds), Chemical Engineer's Handbook, 5$^{th}$ Edition (1973) Chapter 4, McGraw-Hill, NY). The pretreatment may be carried out as a batch process, or as a continuous process. Alternatively, the biomass, water and nucleophilic base may be combined in one vessel, then transferred to another reactor. Also biomass may be pretreated in one vessel, then further processed in another reactor.

In order to obtain sufficient quantities of sugars from biomass, the biomass may be pretreated with water and at least one nucleophilic base either once or several times. Likewise, the combined hydrolysis of xylan with dilute acid followed by enzymatic saccharification can be performed one or more times. Both pretreatment and hydrolysis/saccharification processes may be repeated if desired to obtain higher yields of sugars. To assess performance of the pretreatment and hydrolysis/saccharification processes, separately or together, the theoretical yield of sugars derivable from the starting biomass can be determined and compared to the measured yields.

Hydrolysis and Saccharification

Following pretreatment of the provided biomass with water and at least one nucleophilic base, the polysaccharide enriched biomass comprises a mixture of nucleophilic base, water, partially degraded biomass, lignin, polysaccharides, and monosaccharides. The mixture comprises a solid (insoluble) fraction and a liquid (soluble) fraction. The solid fraction comprises biomass in which the non-carbohydrate component has been significantly reduced. The liquid fraction is composed of lignin and its fragments as its metal salt, along with the excess base and salts related to the nucleophilic base. Prior to saccharification, at least a portion of the solid fraction of the polysaccharide enriched biomass may be isolated in order to physically separate it from the lignin-containing liquid fraction. Isolation of as much of the solid fraction as possible is advantageous, as this allows higher yield of sugars to be obtained after saccharification.

In some of the methods described herein, the composition of the isolated solid fraction of the polysaccharide enriched biomass, on a dry weight basis, may be greater than about 75% polysaccharide or greater than about 80% polysaccharide or greater than about 85% polysaccharide or greater than about 90% polysaccharide.

Methods for separating the solid fraction from the liquid fraction include, but are not limited to, decantation, filtration, and centrifugation. Methods of filtration include, for example, belt filtration, vacuum filtration, and pressure filtration. Optionally, at least a portion of the solid fraction may be recycled to the pretreatment reactor. The solid fraction may optionally be washed with an aqueous solvent (e.g., water) to remove adsorbed lignin prior to being recycled to the pretreatment reactor. The solid fraction may then re-subjected to additional treatment with at least one nucleophilic base as described above for pretreatment, followed by saccharification with a saccharification enzyme consortium.

The liquid fraction may optionally be used as an energy source, or some of the desirable components contained in it may be isolated for additional uses.

The isolated solid fraction of the polysaccharide enriched biomass may be contacted with an aqueous acid solution comprising at least one mineral acid at a temperature and for a reaction time sufficient to produce an intermediate saccharification product. The mineral acid preferentially hydrolyzes the xylan. The intermediate saccharification product comprises xylose, xylan, and glucan. In some of the methods described herein, at least about 40 percent, or at least about 50 percent, of the xylan in the isolated solid fraction of the polysaccharide enriched biomass may be hydrolyzed in the intermediate saccharification product.

The amount of the polysaccharide enriched biomass solid fraction used in contacting the aqueous acid solution may be from about 5 weight percent to about 30 weight percent, for example from about 10 weight percent to about 25 weight percent, or for example from about 13 weight percent to about 20 weight percent, based on the total weight of the aqueous acid solution and the polysaccharide enriched biomass solid fraction. The biomass concentration may be maximized to the extent possible to minimize the volume of the reaction vessel and to minimize the total volume of material in the acid-catalyzed hydrolysis step, making the process more economical. From a practical viewpoint, high ratios of the weight of solid polysaccharide enriched biomass to the weight of the aqueous acid solution may be limited by the ability to provide sufficient mixing, or intimate contact, for xylan hydrolysis to occur at a practical rate.

The aqueous acid solution comprises at least one mineral acid. The mineral acid is selected from the group consisting of sulfuric acid, phosphoric acid, hydrochloric acid, nitric acid, or a combination thereof. Useful concentrations of the mineral acid in the aqueous acid solution are generally about 0.1 wt % to about 5 wt % acid, for example about 0.5 wt % to about 3 wt % acid. The concentration of the mineral acid in the aqueous acid solution may be sufficiently dilute that neither the acid nor its salts need to be removed from the hydrolyzate prior to fermentation of the sugars.

The acid-catalyzed hydrolysis may be performed at a temperature of about 70° C. to about 160° C., for example from about 90° C. to about 150° C. The hydrolysis reaction time may be from about 10 minutes to about 200 minutes, for example from about 10 minutes to about 40 minutes.

After the acid-catalyzed hydrolysis, the intermediate saccharification product may be contacted with a saccharification enzyme consortium at a pH and a temperature sufficient to produce a saccharification product comprising at least about 7 percent by weight fermentable sugars in 24 hours of contact with the saccharification enzyme consortium.

Prior to saccharification, the intermediate saccharification product may be treated to alter the pH, composition or temperature such that the enzymes of the saccharification enzyme consortium will be active. The pH may be altered through the addition of bases in solid or liquid form. The temperature may be brought to a temperature that is compatible with saccharification enzyme activity, as noted below. Any cofactors required for activity of enzymes used in saccharification may be added.

The intermediate saccharification product is then further hydrolyzed in the presence of a saccharification enzyme consortium to release oligosaccharides and/or monosaccharides in a hydrolyzate. For example unreacted xylan is converted to xylose and glucan is converted to glucose. Saccharification enzymes and methods for biomass treatment are reviewed in Lynd, L. R., et al. (Microbiol. Mol. Biol. Rev. (2002) 66:506-577).

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.).

Glycosidases useful in the methods described herein can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Novozyme 188. In addition, saccharification enzymes may be produced biologically, including using recombinant microorganisms.

Preferably the saccharification reaction is performed at or near the temperature and pH optima for the saccharification enzymes. The temperature optimum used with the saccharification enzyme consortium in the present method may range from about 15° C. to about 100° C. In the methods described herein, the temperature optimum may range from about 20° C. to about 80° C. or from about 30° C. to about 60° C. or from about 45° C. to about 55° C. The pH optimum may range from about 4 to about 6 or from about 4.5 to about 5.5 or from about 4.5 to about 5.0.

The saccharification may be performed for a time of about several minutes to about 168 hours, for example from about several minutes to about 48 hours. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium. These variables may be adjusted as necessary to obtain an optimal saccharification product for use in fermentation.

The saccharification may be performed batch-wise or as a continuous process. The saccharification may also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The final saccharification product comprises sugars, wherein the sugars comprise at least one sugar monomer selected from the group consisting of glucose, arabinose, xylose, mannose, and galactose or a combination thereof. The final saccharification product may comprise at least about 7 percent by weight fermentable sugars, based on the total weight of the saccharification product, in 24 hours of contact with the saccharification enzyme consortium; or at least about 12 percent by weight fermentable sugars in 72 hours of contact with the saccharification enzyme consortium. The concentration of the solid fraction of the polysaccharide enriched biomass in the aqueous suspension for saccharification may be from about 10 weight percent to about 20 weight percent, or for example from about 13 weight percent to about 20 weight percent, and the final saccharification product may comprise sugars corresponding to at least a 65% saccharification yield, based on the sum of glucan and xylan in the polysaccharide enriched biomass.

The acid-catalyzed hydrolysis and enzymatic saccharification reactions may be performed in any suitable vessel, such as a batch reactor a continuous reactor. The suitable vessel may be equipped with a means, such as impellers, for agitating the biomass/acid mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, NY). It is advantageous to perform the saccharification reaction in the same vessel as the acid-catalyzed hydrolysis is performed.

The degree of solubilization of sugars from biomass following acid-catalyzed hydrolysis and saccharification may be monitored by measuring the release of monosaccharides and oligosaccharides. Methods to measure monosaccharides and oligosaccharides are well known in the art. For example, the concentration of reducing sugars may be determined using the 1,3-dinitrosalicylic (DNS) acid assay (Miller, G. L., Anal. Chem. (1959) 31:426-428). Alternatively, sugars may be measured by HPLC using an appropriate column as described herein in the General Methods section.

Fermentation to Target Products:

The polysaccharide enriched (a.k.a. readily saccharifiable) biomass produced by the present methods may be hydrolyzed by enzymes as described above to produce fermentable sugars which then can be fermented into a target product. "Fermentation" refers to any fermentation process or any process comprising a fermentation step. Target products include, without limitation alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., Biocommodity Engineering, Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980).

Potential coproducts may also be produced, such as multiple organic products from fermentable carbohydrate. Lignin-rich residues remaining after pretreatment and fermentation can be converted to lignin-derived chemicals, chemical building blocks or used for power production.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, G. P., in *Handbook on Bioethanol: Production and Utilization*, Wyman, C. E., ed., Taylor & Francis, Washington, D.C., 179-212, 1996). SSCF includes the cofermentation of multiple sugars (Sheehan, J., and Himmel, M., Bioethanol, Biotechnol. Prog. 15: 817-827, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., Microbiol. Mol. Biol. Reviews, 66: 506-577, 2002).

These processes may be used to produce target products from the polysaccharide enriched (a.k.a. readily saccharifiable)/biomass produced by the pretreatment methods described herein.

EXAMPLES

The methods described herein are further illustrated by the following examples.

The following materials were used in the examples. All commercial reagents were used as received. Sulfuric acid, ammonium hydroxide, acetic acid, acetamide, yeast extract, glucose, xylose, sorbitol, MgSO4.7H2O, phosphoric acid and citric acid were obtained from Sigma-Aldrich (St. Louis, Mo.).

Corn cob was purchased from Independence Corn By Products (ICBP Cob), Independence, Iowa. The seller stored the cob at 60° C. and milled and sieved the cob to ⅛". The dry mass content of the cob was about 92.5%. Another variety of cob referred to as MDO7 cob was obtained from University of Wisconsin Farm, in Madison, Wis. and was milled to assorted sizes.

The following abbreviations are used: "HPLC" is High Performance Liquid Chromatography, "C" is Centigrade, "kPa" is kiloPascal, "m" is meter, "mm" is millimeter, "kW" is kilowatt, "μm" is micrometer, "μL" is microliter, "mL" is milliliter, "L" is liter, "min" is minute, "mM" is millimolar, "cm" is centimeter, "g" is gram(s), "mg" is milligrams, "kg" is kilogram, "wt" is weight, "wt %" means weight percent "h" is hour(s), "d" is day(s), "temp" or "T" is temperature, "theoret" is theoretical, "pretreat" is pretreatment, "DWB" is dry weight of biomass, "ASME" is the American Society of Mechanical Engineers, "s.s." is stainless steel.

Carbohydrate Analysis of Biomass

A modified version of the NREL LAP procedure "Determination of Structural Carbohydrates and Lignin in Biomass" was used to determine the weight percent glucan and xylan in the biomass. Sample preparation was simplified by drying at 80° C. under vacuum or at 105° C. under ambient pressure overnight. The samples were knife milled to pass through a 20 mesh screen but were not sieved. The dry milled solids were than subjected to the acid hydrolysis procedure at a 50 mg solids scale. The solids were not first extracted with water or ethanol. HPLC analysis of sugars was done on an Aminex HPX-87H column and no analysis of lignin was attempted.

The soluble sugars glucose, cellobiose, and xylose in saccharification liquor were measured by HPLC (Waters Alliance Model, Milford, Mass.) using Bio-Rad HPX-87H column (Bio-Rad Laboratories, Hercules, Calif.) with appropriate guard columns, using 0.01 N aqueous sulfuric acid as the eluant. The sample pH was measured and adjusted to 5-6 with sulfuric acid if necessary. The sample was then passed through a 0.2 μm syringe filter directly into an HPLC vial. The HPLC run conditions were as follows:

Biorad Aminex HPX-87H (for carbohydrates):
  Injection volume: 10-50 μL, dependent on concentration and detector limits
  Mobile phase: 0.01 N aqueous sulfuric acid, 0.2 micron filtered and degassed
  Flow rate: 0.6 mL/minute
  Column temperature: 50° C., guard column temperature<60° C.
  Detector temperature: as close to main column temperature as possible
  Detector: refractive index
  Run time: 15 minute data collection After the run, concentrations in the sample were determined from standard curves for each of the compounds.

General Procedure for Delignification of Corn Cob

Corn cob was suspended in a specified volume of deionized water containing a specified weight of nucleophilic base and then mixed with a mechanical stirrer. The slurry was heated to the desired temperature for a specified time. Following this the reaction mixture was cooled to 50° C., vacuum filtered, and the solid residue was washed with deionized water. The solid residue was dried at room temperature either under ambient condition or laboratory vacuum (20 mm Hg). The dry mass content of the solid residue was determined by weighing a known weight of sample and heating to 99° C. under nitrogen atmosphere until constant weight was achieved.

Example 1

Delignification of Corn Cob

Corn cob (MDO7, 2.5 kg, moisture content 10%) was slowly added to a stirred solution of 2% sodium hydroxide solution (10 L). The amount of sodium hydroxide (NaOH) was 8.0 weight percent relative to the weight of corn cob. The initial pH of the solution was 12.3. The mixture was heated to reflux and maintained under reflux for 20 h. The reaction mixture was allowed to cool to 60° C. The reaction pH at this point was 9.80. A portion of the mixture (200 g) was set aside. The remainder of the mixture was transferred to a filter funnel with the aid of additional 1.9 kg water and filtered under laboratory vacuum. The filtrate was kept separately for analysis. The solid residue from the filtration was washed with water (4×5 L) and re-suspended in deionized water (10 L). The pH of the suspension was maintained at 5.0 for 2 hours by one addition of 37% HCl (2.5 mL). The suspension was then filtered. After draining off most of the liquid, the solid was collected and stored at room temperature.

The weight of the solid recovered was 5.31 kg. A portion of the solid was dried at 99° C. under nitrogen atmosphere for 4 h to determine the dry matter content of the cake, which was determined to be 25.9%. Further drying of the cake prior to saccharification was done under atmospheric pressure and at ambient temperature for 4 days.

The glucan and xylan content of the cob before and after delignification was determined by the NREL methods, well established in the art, and were found to be as follows:
Raw cob=39.2 wt % glucan; 28 wt % xylan
Delignified cob=51 wt % glucan, 38 wt % xylan
The weight ratio of glucan to xylan in the raw cob was 1.40. The weight ratio of glucan to xylan in the delignified cob was 1.34.

Example 2

Delignification of Corn Cob by Treatment with 5.1, 8.0 and 20.0% wt % Sodium Hydroxide Relative to Weight of Cob 5.1% Sodium hydroxide treatment (5.1 wt % NaOH relative to weight of cob): Corn cob (ICBP, 100 g, milled to 2 mm) was suspended in 0.85% aqueous sodium hydroxide (200 mL, pH 13.0) and heated to 110° C. for 18 h. When the pH was checked at this time, it was nearly neutral. Another 200 mL of 0.85% aqueous sodium hydroxide and solid sodium hydroxide (1.7 g) were added and the heating was continued with occasional shaking of the flask. After 24 h, the hot solution was filtered and extensively washed with water. Though brown color eluted out with the filtrate, the solid material was brown colored indicating the presence of lignin adsorbed to the material. Also, the corn cob pellets retained their shape without as much chemical milling occurring as seen in pretreatment with higher concentrations of NaOH solution. The residue was suspended in water and the pH of the solution was adjusted to pH 5.0 with 20% aqueous citric acid. The residue was filtered and dried at room temperature under laboratory vacuum for 24 h. Yield of solid was 70.3 g. The sample was determined to have 6% moisture content.

8.0% Sodium hydroxide treatment (8.0 wt % NaOH relative to weight of cob): Corn cob (ICBP, 100 g, milled to 2 mm) was suspended in 2% aqueous sodium hydroxide and heated to 110° C. for 24 h. The solution was filtered hot and the residue washed with water to neutral pH and dried under laboratory vacuum for 48 h. The weight of pale yellow powder was 79.3 g. The moisture content of the solid was 20%.

A portion of the dried solid (42.0 g) was suspended in water (500 mL) and the pH (9.5) was lowered to 5.0 by the addition of 10% aqueous citric acid solution. After 45 min at this pH the suspension was filtered, washed with water and dried under laboratory vacuum. The moisture content of this material was 7%.

20.0% Sodium hydroxide treatment (20.0 wt % NaOH relative to weight of cob): Corn cob (ICBP, 1000 g, milled to 2 mm size) was suspended in 5% aqueous sodium hydroxide (4000 mL) and heated to 110° C. for 16 h. The dark brown liquid was filtered hot and much of the liquid on the solid was drained under laboratory vacuum. The solid residue on the filter was washed with water until no more color eluted out. The solid was dried under laboratory vacuum for 24 hours.

100 gram of the above sample was suspended in water (700 mL) and stirred. The pH of the solution was 11.2. Aqueous citric acid solution (10%) was added to lower the pH to 5.0 and the suspension was stirred for 30 min. The solid was then filtered, washed with water and dried under vacuum at room temperature for 24 hours. After drying, 86.2 g of polysaccharide enriched biomass was obtained. The moisture content of this material was 7.3 wt %.

Glucan/xylan ratios, glucan wt %, xylan wt %, lignin wt %, and the percentage total carbohydrate content before and after sodium hydroxide treatment, as determined by the NREL methods for carbohydrate analysis, are presented in Table 1.

The pretreatments with 5.1 and 8.0 weight percent NaOH relative to the weight of the biomass used show delignification of the biomass while maintaining a glucan/xylan weight ratio within 15% of that for the untreated biomass.

TABLE 1

Results for Polysaccharide Enriched Biomass Obtained by NaOH Pretreatments (Example 2).

| Sample | Glucan/Xylan weight Ratio | Glucan (wt %) | Xylan (wt %) | Lignin (wt %) | % Total Carbohydrate in the Biomass |
|---|---|---|---|---|---|
| Untreated corn cob | 1.33 | 37.5 | 28.74 | 13.88 | 66 |
| 5.1% NaOH | 1.33 | 47.8 | 35.8 | ND [1] | 84 |
| 8.0% NaOH | 1.35 | 52.96 | 39.11 | 3.33 | 92 |
| 20% NaOH | 1.84 | 58.55 | 31.86 | 5.43 | 90 |

Note:
[1] ND means "not determined"

Example 3

Combined Chemical & Enzymatic Hydrolysis of Delignified Corn Cob to Produce Fermentable Sugars Delignification of corn cob: Corn cob (1000 g, 2 mm size) was suspended in 2% aqueous sodium hydroxide (4000 mL) and heated to 110° C. for 24 h. The solution was filtered hot and the reaction mixture filtrates were set aside. The solids that collected in the funnel were washed with water until the pH was neutral and the filtrate was colorless. The solid was dried under laboratory vacuum for 48 h. The solid (990 g) had 37% moisture, corresponding to a dry mass weight of 624 g.

The above solid was suspended in water (2500 mL) and the pH of the suspension was adjusted from 8.65 to 5.00 by the addition of 20% aqueous citric acid. This mixture was filtered and the solid was dried under house vacuum for 24 h, yielding a partially dried delignified corn cob (2011.9 g), moisture content 66%, dry mass content 681.2 g. To remove any dissolved solid, the solid was resuspended in deionized water (4000 mL), the water drained and the residue dried under laboratory vacuum for 18 h, yielding a partially dried corn cob (1832.3 g, moisture content 67%, dry mass content 598.3 g). The glucan and xylan contents of this residue was 56.2% and 36.7%, respectively.

Acid hydrolysis, followed by enzymatic hydrolysis of delignified corn cob: Delignified cob (33% solid content, 3.0 g) was placed in each of six 10 mL microwavable vials (6 identical samples). Aqueous 5.5 weight % sulfuric acid (0.75 mL) was added to the first three vials and aqueous 10 weight % phosphoric acid was added to vials 4 to 6. Additionally, 2 mL of deionized water was added to each vial. The vials were conveniently heated to 140° C. in a microwave reactor and the pressure of each reaction vial was recorded as follows.

| Vials | Reaction Time | Temp | Pressure |
|---|---|---|---|
| 1 | 10 min | 140° C. | 6 bar |
| 2 | 20 min | 140° C. | 6 bar |
| 3 | 40 min | 140° C. | 6 bar |
| 4 | 10 min | 140° C. | 6 bar |
| 5 | 20 min | 140° C. | 6 bar |
| 6 | 40 min | 140° C. | 6 bar |

After microwave irradiation for the specified duration, samples (100 μL) were taken of each vial and were analyzed by HPLC for the production of glucose and xylose. Then the pH of the reaction vials 1 to 6 was raised to 5.0 by the addition of aqueous 20 weight % sodium hydroxide. The total volume of the liquid in the reaction samples were adjusted with 50 mM sodium citrate buffer (1.5 mL, pH 5.0) and left at room temperature overnight. This was then followed by enzymatic saccharification by the addition of Spezyme® CP cellulase (Genencor International, Rochester N.Y.) (100 μL, protein concentration 150 mg/mL) and Novozyme 188 (Novo Nordisk, Princeton, N.J.) (100 μL, protein concentration 50.6 mg/mL) to samples 1-6 and incubating these samples at 50° C. After 24, 46, and 72 h, samples were analyzed by HPLC for glucose and xylose content. At the completion of the reaction (72 h), the reaction mixture was filtered to estimate the remaining insoluble residue. The soluble product in the filtrate was analyzed by NMR and determined to be as follows:

| Sample | Wt. Insoluble Residue (mg) |
| --- | --- |
| 1 | 159 |
| 2 | 100 |
| 3 | 26 |
| 4 | 154 |
| 5 | 243 |
| 6 | 164 |

TABLE 2

Saccharification yield of delignified corn cob treated with aqueous 0.87% sulfuric acid or 1.58 weight % phosphoric acid for 10, 20, and 40 min at 140° C., followed by enzymatic saccharification at pH 5.0.
SACCHARIFICATION PERCENT YIELD

| Reaction | Acid | Acid Hydrolysis Reaction Time (min) | Component | Enzymatic Saccharification Reaction Time (h) | | |
| --- | --- | --- | --- | --- | --- | --- |
| | | | | 0 | 6 | 72 |
| 1 | .87% H2SO4 | 10 | Glucose | 2.2 | 23.6 | 61.8 |
| | | | Xylose | 53.7 | 55.6 | 62.7 |
| | | | Total Sugar | 22.9 | 36.4 | 62.2 |
| 2 | | 20 | Glucose | 2.4 | 24.8 | 70.3 |
| | | | Xylose | 61.7 | 59.2 | 72.2 |
| | | | Total Sugar | 26.3 | 38.6 | 71.0 |
| 3 | | 40 | Glucose | 2.8 | 29.3 | 79.7 |
| | | | Xylose | 59.8 | 65.2 | 75.2 |
| | | | Total Sugar | 25.7 | 43.7 | 77.9 |
| 4 | 1.58% H3PO4 | 10 | Glucose | 9.3 | 19.2 | 55.1 |
| | | | Xylose | 25.3 | 33.6 | 50.6 |
| | | | Total Sugar | 15.7 | 25.0 | 53.3 |
| 5 | | 20 | Glucose | 11.1 | 22.6 | 52.5 |
| | | | Xylose | 38.9 | 42.8 | 54.2 |
| | | | Total Sugar | 22.2 | 30.7 | 53.1 |
| 6 | | 40 | Glucose | 10.1 | 23.3 | 61.8 |
| | | | Xylose | 37.6 | 46.3 | 61.6 |
| | | | Total Sugar | 21.2 | 32.5 | 61.7 |

Samples were analyzed after acid treatment (0 h) and after 6 h and 72 h of enzymatic treatment.

TABLE 3

Sugar titer of delignified corn cob treated with aqueous 0.87% sulfuric acid or 1.58 weight % phosphoric acid for 10, 20, and 40 min at 140° C., followed by enzymatic saccharification at pH 5.0.

| | | | % Sugar | | |
| --- | --- | --- | --- | --- | --- |
| | | Acid Hydrolysis | Enzymatic Saccharification Reaction Time (h) | | |
| Reaction | Acid | Reaction Time (min) | 0 | 6 | 72 |
| 1 | .87% H2SO4 | 10 | 5.0 | 5.6 | 9.6 |
| 2 | | 20 | 5.7 | 5.9 | 10.9 |
| 3 | | 40 | 5.6 | 6.7 | 12.0 |
| 4 | 1.58% H3PO4 | 10 | 3.4 | 3.8 | 8.2 |
| 5 | | 20 | 4.8 | 4.7 | 8.2 |
| 6 | | 40 | 4.6 | 5.0 | 9.5 |

Samples were analyzed after acid treatment (0 h) and after 6 h and 72 h of enzymatic treatment.

All the runs performed using sulfuric acid for the hydrolysis of delignified corn cob showed more than 50 percent hydrolysis of the xylan originally present in the delignified corn cob (the isolated polysaccharide enriched biomass). Maximum chemical and enzymatic digestion of the delignified corn cob and highest sugar content was observed in Sample 3 heated with sulfuric acid for 40 minutes, followed by enzymatic treatment.

Example 4

Combined Chemical & Enzymatic Hydrolysis of Delignified Corn Cob to Produce Fermentable Sugars Delignification of corn cob: Corn cob (ICBP cob, 1000 g, 2 mm size) was delignified following the procedure of Example 3.

Acid hydrolysis, followed by enzymatic hydrolysis of delignified corn cob: Delignified cob (33% solid content, 3.0 g) was placed in each of six 10 mL microwavable vials (6 identical samples). Aqueous 5.5 weight % sulfuric acid (1.50 mL) was added to the first three vials and aqueous 10 weight % phosphoric acid (1.5 mL) was added to vials 4 to 6. Additionally, 1.5 mL of deionized water was added to each vial. The vials were conveniently heated to 140° C. in a microwave reactor and the pressure of each reaction vial was recorded as follows.

| Vials | Reaction Time | Temp | Pressure |
| --- | --- | --- | --- |
| 1 | 10 min | 140° C. | 6 bar |
| 2 | 20 min | 140° C. | 6 bar |
| 3 | 30 min | 140° C. | 6 bar |
| 4 | 10 min | 140° C. | 6 bar |
| 5 | 20 min | 140° C. | 6 bar |
| 6 | 30 min | 140° C. | 6 bar |

After microwave irradiation for the specified duration, samples (100 μL) were taken of each vial and were analyzed by HPLC for the production of glucose and xylose. Then the pH of the reaction vials 1 to 6 were raised to 5.0 by the addition of aqueous 20 weight % sodium hydroxide. The total volume of the liquid (6.50 mL) in the reaction samples were adjusted with 50 mM sodium citrate buffer (1.5 mL, pH 5.0) and left at room temperature overnight. This was then followed by enzymatic saccharification by the addition of Spezyme® CP cellulase (100 µL, protein concentration 150 mg/mL) and Novozyme 188 (100 µL, protein concentration 50.6 mg/mL) to samples 1-6 and incubating these samples at 50° C. After 24, 46, and 72 h, samples were analyzed by HPLC for glucose and xylose content. At the completion of the reaction (72 h), the reaction mixture was filtered to estimate the remaining insoluble residue. The soluble product in the filtrate was analyzed by NMR. Maximum chemical and enzymatic digestion of the delignified corn cob and highest sugar content was observed in Sample 3 heated with sulfuric acid for 40 minutes, followed by enzymatic treatment.

TABLE 4

The amount of glucose, xylose and total monomeric (glucose and xylose) produced in the combined chemical and enzymatic hydrolysis of delignified corn cob treated with aqueous 1.7% sulfuric acid or 3.0 weight % phosphoric acid for 10, 20, and 30 min at 140° C., followed by enzymatic saccharification at pH 5.0.
Total Monomer Sugar Mass (mg)

| Sugar | Acid Hydrolysis Acid | Reaction Time (min) | Enzymatic Saccharification Reaction Time (d) 0 d | 1 d | 2 d | 3 d |
|---|---|---|---|---|---|---|
| Glucose | 1.7% H2SO4 | 10 | 16.2 | 238.0 | 276.7 | 344.4 |
|  |  | 20 | 19.1 | 223.0 | 327.9 | 382.6 |
|  |  | 30 | 21.5 | 291.1 | 366.4 | 444.9 |
|  | 3% H3PO4 | 10 | 0.0 | 189.0 | 229.3 | 268.0 |
|  |  | 20 | 7.7 | 224.5 | 312.2 | 291.5 |
|  |  | 30 | 8.4 | 229.9 | 306.1 | 284.1 |
| Xylose | 1.7% H2SO4 | 10 | 260.3 | 276.5 | 249.3 | 286.1 |
|  |  | 20 | 288.7 | 278.4 | 310.0 | 330.3 |
|  |  | 30 | 302.1 | 322.9 | 325.2 | 354.4 |
|  | 3% H3PO4 | 10 | 180.4 | 189.3 | 174.4 | 182.2 |
|  |  | 20 | 214.5 | 227.7 | 246.2 | 264.7 |
|  |  | 30 | 207.0 | 230.7 | 244.5 | 293.5 |
| Glucose + Xylose | 1.7% H2SO4 | 10 | 276.5 | 514.5 | 526.1 | 630.5 |
|  |  | 20 | 307.8 | 501.4 | 637.9 | 712.9 |
|  |  | 30 | 323.6 | 614.0 | 691.6 | 799.3 |
|  | 3% H3PO4 | 10 | 180.4 | 378.3 | 403.7 | 450.2 |
|  |  | 20 | 222.2 | 452.1 | 558.4 | 556.1 |
|  |  | 30 | 215.4 | 460.6 | 550.5 | 577.5 |

Samples were analyzed after acid treatment (0 h) and after 1 d, 2 d and 3 days of enzymatic treatment

TABLE 5

Saccharification yield of delignified corn cob treated with aqueous 1.7% sulfuric acid or 3.0 weight % phosphoric acid for 10, 20, and 30 min at 140° C., followed by enzymatic saccharification at pH 5.0.
Saccharification % Yield

| Sugar | Acid Hydrolysis Acid | Reaction Time (min) | Enzymatic Saccharification Reaction Time (d) 0 d | 1 d | 2 d | 3 d |
|---|---|---|---|---|---|---|
| Glucose | 1.7% H2SO4 | 10 | 2.6 | 38.5 | 44.8 | 55.8 |
|  |  | 20 | 3.1 | 36.1 | 53.1 | 61.9 |
|  |  | 30 | 3.5 | 47.1 | 59.3 | 72.0 |
|  | 3% H3PO4 | 10 | 0.0 | 30.6 | 37.1 | 43.4 |
|  |  | 20 | 1.2 | 36.3 | 50.5 | 47.2 |
|  |  | 30 | 1.4 | 37.2 | 49.6 | 46.0 |
| Xylose | 1.7% H2SO4 | 10 | 62.9 | 66.7 | 60.2 | 69.1 |
|  |  | 20 | 69.7 | 67.2 | 74.8 | 79.7 |
|  |  | 30 | 72.9 | 78.0 | 78.5 | 85.6 |
|  | 3% H3PO4 | 10 | 43.6 | 45.7 | 42.1 | 44.0 |
|  |  | 20 | 51.8 | 55.0 | 59.4 | 63.9 |
|  |  | 30 | 50.0 | 55.7 | 59.0 | 70.9 |
| Glucose + Xylose | 1.7% H2SO4 | 10 | 26.8 | 49.9 | 51.0 | 61.1 |
|  |  | 20 | 29.8 | 48.6 | 61.8 | 69.1 |
|  |  | 30 | 31.4 | 59.5 | 67.0 | 77.5 |
|  | 3% H3PO4 | 10 | 17.5 | 36.7 | 39.1 | 43.6 |
|  |  | 20 | 21.5 | 43.8 | 54.1 | 53.9 |
|  |  | 30 | 20.9 | 44.6 | 53.4 | 56.0 |

Samples were analyzed after acid treatment (0 h) and after 1 d, 2 d and 3 days of enzymatic treatment.

All the runs showed more than 50 percent hydrolysis of the xylan originally present in the delignified corn cob (the isolated polysaccharide enriched biomass) at the acid concentrations used for Example 4. Maximum chemical and enzymatic digestion of the delignified corn cob and highest sugar content was observed in Sample 3 heated with sulfuric acid for 30 minutes, followed by enzymatic treatment.

The combination of chemical and enzymatic hydrolysis in one method for converting polysaccharides to monosaccharides provides several advantages over the individual approaches of acid catalyzed hydrolysis or enzymatic saccharification. In the combined chemical and enzymatic process, the saccharification uses less enzymes to obtain high saccharification yield for each milligram of enzyme used. This process can dramatically increase the enzyme efficiency, reduce the cost of the hydrolysis step, and afford fermentable sugars in high concentration while avoiding the formation of detrimental impurities.

What is claimed is:

1. A method of producing a concentrated sugar solution from biomass, the method comprising:
    a) delignifying biomass comprising the substeps of
        i) contacting with water and at least one nucleophilic base, a biomass comprising lignin and having a glucan/xylan weight ratio $G_1/X_1$ to form a biomass slurry having a pH of about 12.5 to about 13.0; and
        ii) maintaining the biomass slurry under reaction conditions such that the slurry attains a pH of about 9.5 to about 10.0 and has a glucan/xylan weight ratio $G_2/X_2$ within about 15% of the value of $G_1/X_1$, and wherein the slurry comprises a lignin-containing liquid fraction and a solid fraction comprising a polysaccharide enriched biomass;
        wherein $G_1$ and $G_2$ are grams of glucan per 100 grams of biomass and biomass slurry respectively, and $X_1$ and $X_2$ are grams of xylan per 100 grams of biomass and biomass slurry respectively;
    b) contacting with an aqueous acid solution comprising at least one mineral acid the solid fraction of the polysaccharide enriched biomass at reaction conditions sufficient to produce an intermediate saccharification product comprising xylose, xylan, and glucan, wherein the concentration of the solid fraction in the aqueous acid solution is about 13 weight percent to about 20 weight percent; and
    c) contacting with a saccharification enzyme consortium at a pH of from about 4.5 to about 5.5 the intermediate saccharification product at reaction conditions sufficient to produce a final saccharification product comprising at least about 7 percent by weight fermentable sugars, based on the total weight of the saccharification product, in 24 hours of contact with the saccharification enzyme consortium.

2. The method of claim 1, wherein the at least one nucleophilic base comprises a water soluble metal hydroxide, optionally in combination with a metal carbonate or an organic hydroxide.

3. The method of claim 1, wherein the reaction conditions sufficient to produce a polysaccharide enriched biomass include a temperature from about 20° C. to about 110° C. and a reaction time from about 4 hours to about 30 days.

4. The method of claim 1, wherein the value of $G_2/X_2$ is within 10% of the value of $G_1/X_1$.

5. The method of claim 1, further comprising isolating at least a portion of the polysaccharide enriched biomass solid fraction.

6. The method of claim 1, wherein the at least one mineral acid is selected from the group consisting of sulfuric acid, phosphoric acid, hydrochloric acid, nitric acid, and a combination of these.

7. The method of claim 6, wherein the concentration of the mineral acid in the aqueous acid solution is about 0.1 weight percent to about 5 weight percent.

8. The method of claim 1, wherein the reaction conditions sufficient to produce an intermediate saccharification product include a temperature from about 70° C. to about 160° C.

9. The method of claim 1, wherein the reaction conditions sufficient to produce an intermediate saccharification product include a reaction time from about 10 minutes to about 200 minutes.

10. The method of claim 1 or 5, wherein at least about 50 percent of the xylan in the solid fraction of the polysaccharide enriched biomass is hydrolyzed in the intermediate saccharification product.

11. The method of claim 1, wherein the final saccharification product comprises at least about 12 percent by weight sugars in 72 hours.

12. The method of claim 1 or 5, wherein the composition of the solid fraction of the polysaccharide enriched biomass, on a dry weight basis, is greater than about 80% polysaccharide.

13. The method of claim 1, wherein the final saccharification product comprises at least one sugar monomer selected from the group consisting of glucose, arabinose, xylose, mannose, galactose, and a combination of these.

* * * * *